United States Patent
Brandon et al.

(10) Patent No.: US 8,772,389 B1
(45) Date of Patent: Jul. 8, 2014

(54) COLOR CHANGING CAULK

(75) Inventors: Larry G. Brandon, Adair, OK (US); Michael Gabel, Claremore, OK (US); Curtis True, Pryor, OK (US); Lori S. Gonzales, Pryor, OK (US)

(73) Assignee: Red Devil Incorporated, Tulsa, OK (US)

( * ) Notice: Subject to any disclaimer, the term of this patent is extended or adjusted under 35 U.S.C. 154(b) by 115 days.

(21) Appl. No.: 13/303,365

(22) Filed: Nov. 23, 2011

Related U.S. Application Data

(60) Provisional application No. 61/417,010, filed on Nov. 24, 2010, provisional application No. 61/417,772, filed on Nov. 29, 2010.

(51) Int. Cl.
    *C08K 5/00*    (2006.01)
    *C08G 73/10*   (2006.01)
    *C07C 37/14*   (2006.01)

(52) U.S. Cl.
    USPC ............................. 524/291; 524/323; 524/324

(58) Field of Classification Search
    USPC .......................................... 524/291, 323, 324
    See application file for complete search history.

(56) References Cited

U.S. PATENT DOCUMENTS 6,531,528 B1 * 3/2003 Kurp ............................. 524/291

OTHER PUBLICATIONS

MIRATEC Treated Exterior Composite TRIM, Technical Bulletin: Caulks, Putties and Fillers, 2009.
PDCA, Painting and Decorating Contractors of America, PDCA P11-Painter's Caulk, Implied Requirements, Scope and Standards of Use, undated, but believed to have been published Apr. 9, 2012.
DAP, Inc., DAP Drytex Spackling Ready to Use Latex Spackling (RTU), Material Safety Data Sheet, MSDS No. 00010420001; Dated May 17, 2007.
Aldrich, Reference: Polymer Properties, Polymer Products from Aldrich, Catalog Nos. Z41,247-3 Z41,255-4, Z22,171-6, Z40.603-1 and Z22,195-3 in the Book section, undated, but believed to have been published Sep. 23, 1999.
Arkema Inc., Arkema Emulsion Systems Latex Line, Polymer Selection Guide, pp. 1-12, 2010.
ASTM Int'l, Desigation: C475/C475M-12, Standard Specification for Joint Compound and Joint Tape for Finishing Gypsum Board, Dept of Defense, pp. 1-2, approved Sep. 1, 2012, publ'd Oct. 2012.
ASTM Int'l, Desigation: C920-14, Standard Specification for Elastomeric Joint Sealants, Dept of Defense, pp. 1-4, approved Jan. 1, 2014, publ'd Jan. 2014.

* cited by examiner

*Primary Examiner* — William Cheung
(74) *Attorney, Agent, or Firm* — McAfee & Taft

(57) ABSTRACT

A caulk composition having a first color upon application and a second color upon formation of a skin, wherein said skin is suitable for application of a surface treatment.

21 Claims, No Drawings

COLOR CHANGING CAULK

CROSS REFERENCE TO RELATED APPLICATION

This application incorporates by reference and claims the benefit of U.S. Provisional Application 61/417,010 filed on Nov. 24, 2010, and U.S. Provisional Application 61/417,772 filed Nov. 29, 2010.

DETAILED DESCRIPTION

The current invention provides a caulking composition which signals when the caulk has sufficiently cured to permit application of a surface treatment to the caulk. As used herein, the term caulking composition shall mean a composition suitable for either caulking or sealing. The inventive formula described herein retains at least a degree of elastomeric behavior and remains flexible after cure. Consequently, once fully cured the inventive formula will elongate under stress and return to approximately its original dimensions once stress is released.

By weight percentage, the compositions typically include 0-1% defoamer, 10-50% acrylic polymer, 1-10% solvent, 1-10% antifreeze, 0.1-5% surfactant, 0.01-5% in-can preservative, 0-5% fungicide, 0.01-5% dispersant, 0-10% thickener, 0-10% pH modifier, 0-5% adhesion promoter, 0.001-5% pH indicator, 15-80% filler, and 0.1-10% pigments.

The color changing caulk composition uses a base emulsion as an adhesive foundation. Suitable base emulsions include but are not limited to acrylic polymer emulsions having a glass-transition temperature (Tg) of about −50° C. (−45.6 F) without supplementary plasticizer. One suitable acrylic emulsion is Chemical Abstracts registry number (CAS No.) 253351-13-2, commercially available from The Dow Chemical Co. under the name RHOPLEX 1950.

The caulk composition may optionally include defoamer to reduce or hinder the formation of foam during mixing. Acceptable defoaming agents include silicone and mineral oil-based defoamers for acrylic latex systems. One suitable defoamer is a mineral water-based non-silicone defoamer identified by CAS No. 74-97-5, commercially available from Hangzhou Harmony Chemical Co., Ltd. under the name CATHAY HL-52.

For improved storage characteristics, the color changing caulk may optionally include antifreeze agents. Acceptable antifreeze agents include, but are not limited to, propylene glycol and ethylene glycol. Although susceptible to biological fouling, propylene glycol exhibits generally friendlier environmentally characteristics over ethylene glycol, which is toxic to humans and animals. Color changing caulk compositions formulated with propylene glycol as an antifreeze agent have withstood up to five cycles of freeze/thaw.

Acceptable solvents for the emulsion include mineral spirits and water. Formulas having water as the only solvent allow compositions which do not require plasticizers. Plasticizer-free formulation are typically lower in Volatile Organic Compounds (VOCs), having less than about 3% by weight and generally lower than about 1.5% by weight.

Additionally, the color changing caulk may optionally contain non-ionic surfactants. Surfactants act as emulsifiers during the compounding of the color changing caulk. Suitable non-ionic surfactants include, but are not limited to, ethoxylated alkyl phenol and octylphenoxy polyethoxy ethanol compounds. One suitable surfactant is octoxynol-40, per the International Nomenclature of Cosmetic Ingredients (INCI), commercially available from The Dow Chemical Co. under the name Triton™ X-405.

To increase the package stability of a packaged composition, the color changing caulk composition may optionally include preservatives. Preservatives extend the time during which the caulk composition will generally maintain the desired color shifting functionality and still perform suitably for caulking or sealing purposes. One suitable preservative is 13 dihydroxymethyl 5,5 dimethyl hydantoin, commercially available from Troy Corp. under the name Mergal® 395.

The color changing caulk composition may also optionally include fungicides to combat, lower and/or reduce the growth of mold or mildew on the cured caulk. Acceptable fungicides include carbamate additives, such as 3-iodo-2-propynl butyl carbamate, commercially available from Troy Corp. under the name Polyphase 678. Other fungicides suitable for use in the present invention include, but are not limited to, chlorathalanil compounds.

The color changing caulk composition may include dispersant to prevent settling or clumping of the caulk composition and improve the laying down of a fine bead of caulk. Dispersants improve pigment dispersion and stabilize the composition. Suitable dispersant include, but are not limited to, polycarboxylate sodium salt, dispersants based on hydrophilic and hydrophobic acid copolymers, and phosphates such as potassium tripolyphosphate (KTPP). One suitable dispersant is a polycarboxylate sodium salt pigment dispersant commercially available from The Dow Chemical Co. under the name TAMOL™ 851.

To provide the desired viscosity, the color changing caulk may also include thickeners, such as, but not limited to, alkali-soluble acrylic emulsion copolymer. One suitable anionic thickener is commercially available from The Dow Chemical Co. under the name ACRYSOL™ ASE 60. Other suitable thickeners include, but are not limited to high molecular weight water soluble polymers which causes polymer chain entanglements to occupy large volumes, such as hydroxylethyl cellulose (HEC) and alkali swellable emulsions.

To provide a caulk composition having a pH suitable for yielding the desired color shift, the color changing caulk composition typically includes pH modifiers. Acceptable pH modifiers include aqueous ammonia, amino methyl propanol, aqueous potassium hydroxide solution of 10-30% and aqueous sodium hydroxide solution of 10-30%. Typically, the color changing caulk composition will include a sufficient amount of pH modifiers to yield a pH of about 8-10. Caulks with a pH in this range will be package-stable caulking compositions when stored in the container described herein. One suitable pH modifier is 2-amino 2-methyl 1-propanol, commercially available from The Dow Chemical Co. under the name AMP™-95. While used primarily as a pH modifier, AMP™-95 also aids in dispersion.

To provide the desired color changing characteristic, the color changing caulk includes a sufficient concentration of color changing pH indicator. During the curing process, i.e., upon usage and exposure to the atmosphere, the color changing caulk undergoes a curing process which produces a change in pH. Prior to applying surface treatments to the color changing caulk bead, such as application of oil or water based paints or laquers by spraying or brushing, the bead must have a skin of sufficient thickness to support the surface treatment without damaging the bead. The pH indicator is selected to produce a color change after the calculated time required to provide the desired skin thickness. Thus, the resulting color change signals the degree of cure necessary to form a skin having sufficient strength to accept the application of a surface treatment. Acceptable pH indicators include thymol phthalein, alizarin yellow, thanoate, p-napthobenzein, cresolred, thymol blue, 2,4,6 trinitrotoluene, metacresol purple, and phenolphthalein. Phenolphthalein changes to a pink color in a pH range of about 8.0-12.0 and is colorless below a pH of about 8.

The color changing caulk may also include pigments or fillers to provide whiteness, color, reinforcement, cost reduction and rheology. Pigments or fillers may be selected from ground and precipitated calcium carbonate, titanium dioxide, kaolin clays, talc, mica, and silica, in a variety of particle sizes and morphologies. Formulations having a white final color typically include titanium dioxide. A variety of commercially available dry mix titanium dioxide whiteners are available and may optionally be used. Using a titanium dioxide slurry facilitates a smooth final mixture since titanium dioxide slurries are pre-blended. Acceptable titanium dioxide slurries are acceptably formulated to contain 60-90% $TiO_2$, 10-20% water, 5-10% diethylene glycol, 1-5% surfactant, and 1-5% calcium carbonate. Typically, titanium dioxide slurries are formulated to contain 60-75% $TiO_2$. One suitable pigment is a white pigment having 71% solids and is commercially available from BASF Corp. under the name AURASPERSE® W-308.

When using phenolphthalein as the pH indicator, the color changing caulk composition typically has a pink color upon application. Following exposure to the atmosphere, the pink will gradually change to white as the pH drops during the curing process. The change in color signals the formation of a suitably cured skin appropriate for painting or other surface treatment. The final white coloration following cure is suitable in appearance should conditions preclude surface treatment for a period of time. Alternate pigments may optionally be employed based on the desirability of a different final color.

For many surface treatments, only an adequate skin (rather than complete cure) is required. Consequently, the color changing caulk does not require a complete cure for the color drift indication to occur. Cure time to form the desired skin thickness of the caulk composition typically ranges from about one to four hours. Variables influencing the typical cure time include temperature (cooler conditions prolong curing time), humidity (more humid conditions prolong curing time), bead size (larger beads prolong curing time), tooling (tooled beads cure faster than do untooled beads), and porosity of substrate (less porous substrates prolong curing time). An initially observable color change will occur when the skin has a thickness of about 0.5 mm-1.5 mm. The color change will appear complete when skin has a thickness of about 1 mm-2 mm.

The formulation of the color changing caulk may be adjusted to account for special uses of the caulk requiring differing cure times appropriate for particular surface treatments or other intended post-cure operations. For example, additional pH modifier may be added to the color changing caulk composition to increase the length of post-application curing time needed to obtain the desired pH shift. Alternately, less water may be added to the color changing caulk composition to reduce the volatile migration needed to fully cure. These and other minor adjustments to the color changing caulk composition may be made without undue experimentation and are within the scope of protection intended herein.

The table below provides two columns, the makeup of the one example of the color changing caulk and the allowable range of the illustrative components:

TABLE I

| Material | Example % WT | Allowable Range % WT |
|---|---|---|
| Defoamer (HL-52) | 0.05 | 0-1% |
| Acrylic Polymer (RHOPLEX 1950) | 30.00 | 10-50% |
| Solvent (Water) | 2.9 | 1-10% |
| Antifreeze (Propylene glycol) | 1.00 | 1-10% |
| Surfactant (Ethoxylated alkyl phenol: Triton ™ X-405) | 1.00 | 0.1-5% |
| In-Can Preservative (13 dihydroxymethyl 5,5 dimethyl hydantoin: Mergal ® 395) | 0.05 | 0.01-5% |
| Fungicide (3-Iodo 2-propynyl butyl carbamate: Polyphase 678) | 0.15 | 0-5% |
| Dispersant (Polycarboxylate sodium salt: Tamol ™ 851) | 0.18 | 0.01-5% |
| Additional Dispersant (Potassium tripolyphosphate (KTPP)) | 0.18 | 0-5% |
| Acrylic acid thickener (Ethyl acrylate methyl methacrylate polymer: ACRYSOL ™ ASE 60) | 1.25 | 0-10% |
| pH Modifier (Amino methyl propanol: AMP ™ -95) | 0.9 | 0-10% |
| Adhesion Promoter (Glycidoxy-trimethoxy silane: AP-51) | 0.04 | 0-5% |
| pH Indicator (Phenolphthalein) | 0.10 | 0.001-5% |
| Filler (Calcium carbonate) | 59.70 | 15-80% |
| Pigment ($TiO_2$ slurry: AURASPERSE ® W-308) | 2.50 | 0.1-10% |
| TOTAL: | 100.00 | |

A sample of color changing caulk having the formula of the example described in the above table was tested by examination of a bead of caulk extruded from a standard 10.1 oz. caulking cartridge. A standard bead size of 3/16 in, was extruded from the cartridge and examined for color change in the tooled and untooled state. The color change was observed sooner in a tooled bead than in an untooled bead. Caulk compositions in the tooled state formulated in accordance with the above typically show the desired color change in one to four hours depending on temperature and humidity.

The shelflife of a color changing caulk as used herein means the time during which a packaged caulk composition stored within a temperature range of about 40° F. to about 90° F. (about 4.4° C. to about 32.2° C.) suitably maintain the desired color shifting functionality and still perform suitably for caulking or sealing purposes. To further extend the shelflife, the caulk composition may be packaged under a nitrogen blanket or other inert environment in a container having a mechanical closure. Caulks prepared and packaged in a mechanical closure with a nitrogen blanket typically have a shelflife of at least nine months and preferably at least one year.

Package stability testing was conducted on the color changing caulk using a package constructed from polyethylene containing 10.1 oz. of the color changing caulk composition. After four weeks in a packaged container at 122° F. (50° C.) in a convection oven, the initial pH of the caulk composition was 10. The caulk composition was extruded from the caulk tube after four weeks oven age at 122"F (50° C.) and visually compared to material stored at room temperature for the same period to establish the level of color retention. The caulk composition maintained 70-80% of its original pink color.

One method for producing the color changing caulk composition includes the steps of combining the components under ambient pressure and temperature as follows: (1) addition of the base polymer and defoamer, followed by about five minutes of mixing; (2) addition of water, dispersants, surfactants, preservatives, fungicides, and antifreeze, followed by about five minutes of mixing; (3) addition of a thicker-water blend (1-20% WT of a 1:1 ratio) and adhesion promoters followed by about five minutes of mixing; (4) addition of pH indicator, pH modifier-water blend (1-20% WT of a 1:1 ratio), and filler. The resulting mixture is then mixed under a 20" Hg vacuum minimum pressure at ambient temperature for about thirty minutes.

One method for formulating the color changing caulk begins with the mixer operating at the beginning of the first step. While the mixing order of the ingredients may be altered according to the knowledge of a person having ordinary skill in the art, in the disclosed method the pH indicator is added prior to the addition of the calcium carbonate in order to promote a heterogeneous dispersion of the pH indicator throughout the batch. Mixing temperatures in excess of 100° F. (37.8° C.) will experience volatile loss and are preferably avoided.

A color changing caulk having the formula set forth in Table I was mixed in a conventional mixer capable of maintaining a minimum vacuum of 20" Hg with a high speed disperser and a sweeper blade. Defoamer (HL-52) was introduced into the mixer first, followed by the acrylic polymer (RHOPLEX 1950), solvent (water) and dispersant (KTPP). After mixing the base emulsion for 5 minutes, antifreeze (propylene glycol), surfactant (ethoxylated alkyl phenol), fungicide (3-Iodo 2-propynyl butyl carbamate), and dispersant (polycarboxylate sodium salt) was added. After mixing the ingredients for 5 min, a premixed solution of thickener (ethyl acrylate methyl methacrylate polymer) and water was added. Adhesion promoter (glycidoxy-trimethoxy silane), pH indicator (phenolphthalein), filler (calcium carbonate), and pigment slurry (AURASPERSE® W-308) was next added to the base emulsion. Next, a premixed solution of water and pH modifier (amino methyl propanol) was added and the composition was mixed for another 30 minutes under 20" of Hg minimum vacuum.

Other embodiments of the current invention will be apparent to those skilled in the art from a consideration of this specification or practice of the invention disclosed herein. However, the foregoing specification is considered merely exemplary of the current invention with the true scope and spirit of the invention being indicated by the following claims.

We claim:

1. A caulk composition having a first color upon application and a second color upon formation of a skin, wherein said skin is suitable for application of a surface treatment and wherein said caulk composition remains flexible after it is fully cured wherein said composition comprises a pH indicator which changes color in response to sufficient curing of said composition whereby the degree of cure permits application of a surface treatment to said composition and wherein the pH of said composition having said first color is from about 8 to about 10.

2. The caulk composition of claim 1, wherein said composition is plasticizer-free and once fully cured will elongate under stress and return to approximately its original dimensions once the stress is released.

3. The caulk composition of claim 1, wherein the primary solvent is water.

4. The caulk composition of claim 1, wherein said composition includes a polymer emulsion having a glass transition temperature of about −50° C.

5. The caulk composition of claim 1, wherein said second color is white.

6. The caulk composition of claim 1, wherein the pH of said composition having said second color is below about 8.

7. The caulk composition of claim 1, wherein said skin being suitable for application of a surface treatment has a minimum thickness of about 1 mm-2 mm.

8. A caulk composition comprising an aqueous-based polymer emulsion and a pH indicator wherein prior to use said composition is packaged under an inert environment and has a first color and a pH of from about 8 to about 10 and wherein during use said caulk composition undergoes curing such that it has a second color and a pH of below about 8 and wherein said caulk composition remains flexible after it is fully cured.

9. The caulk composition of claim 8, wherein said composition is plasticizer-free and once fully cured will elongate under stress and return to approximately its original dimensions once the stress is released.

10. The caulk composition of claim 8, wherein the volatile organic compound content of said composition is less than 4% by weight of the post-cure composition.

11. The caulk composition of claim 8, wherein the post-cure composition does not contain ethylene glycol.

12. The caulk composition of claim 8, further comprising at least one filler or pigment selected from a group including calcium carbonate, titanium dioxide, kaolin clays, talc, mica, and silica.

13. The caulk composition of claim 8, wherein the acrylic polymer of said emulsion is the same or substantially the same as that to which Chemical Abstracts registry number 253351-13-2 is assigned.

14. The caulk composition of claim 8, wherein said composition has a shelflife of at least nine months.

15. The caulk composition of claim 8, wherein said composition comprises 0-1 wt % defoamer, 10-50 wt % acrylic polymer, 1-10 wt % solvent, 1-5 wt % dispersant, 1-10 wt % antifreeze, 0.1-5 wt % surfactant, 0.01-5 wt % in-can preservative, 0-5 wt % fungicide, 0-5 wt % additional dispersant, 0-10 wt % thickener, 0-5 wt % adhesion promoter, 0.001-5 wt % pH indicator, 15-80 wt % filler, 0.1-10 wt % pigment and 0-10% pH modifier.

16. The caulk composition of claim 8, further comprising a pH modifier.

17. A method of making a caulk composition, comprising the steps of:
    blending together a base polymer, a preservative, a thickener and a surfactant to form a base emulsion;
    adding a pH indicator to said base emulsion;
    adding at least one filler or pigment selected from a group including calcium carbonate, titanium dioxide, kaolin clays, talc, mica, and silica to said base emulsion; and
    adding a pH modifier to said base emulsion, such that the resulting final composition has a first color and a pH of about 8 to 10; and
    packaging said final composition under an inert blanket environment such that upon use said final composition retains said first color until it is at least partially cured to form a skin and wherein the final composition results in a caulk, which remains flexible after it is fully cured.

18. The method of claim 17, wherein said base polymer is an acrylic polymer emulsion having a glass-transition temperature (Tg) of about −50° C.

19. The method of claim 17, wherein the final composition produced following execution of said steps comprises 0-1 wt % defoamer, 10-50 wt % acrylic polymer, 1-10 wt % solvent, 1-5 wt % dispersant, 1-10 wt % antifreeze, 0.1-5 wt % surfactant, 0.01-5 wt % in-can preservative, 0-5 wt % fungicide, 0-5 wt % additional dispersant, 0-10 wt % thickener, 0-5 wt % adhesion promoter, 0.001-5 wt % pH indicator, 15-80 wt % filler, 0.1-10 wt % pigment and 0-10% pH modifier.

20. The method of claim 19, wherein the final composition produced following execution of said steps comprises from about 30 wt % to 50 wt % acrylic polymer.

21. The caulk composition of claim 15, wherein the composition comprises from about 30 wt % to 50 wt % acrylic polymer.

* * * * *